(12) United States Patent
Casciaro

(10) Patent No.: US 12,369,891 B2
(45) Date of Patent: Jul. 29, 2025

(54) METHOD FOR RENAL CELL CARCINOMA DIAGNOSIS BY MEANS OF ULTRASONIC SIGNALS ANALYSIS AND ULTRASOUND IMAGES

(71) Applicant: Imedicals S.r.l., Lecce (IT)

(72) Inventor: Sergio Casciaro, Lecce (IT)

(73) Assignee: Imedicals S.r.l., Lecce (IT)

( * ) Notice: Subject to any disclaimer, the term of this patent is extended or adjusted under 35 U.S.C. 154(b) by 2 days.

(21) Appl. No.: 18/037,741

(22) PCT Filed: Nov. 24, 2021

(86) PCT No.: PCT/IB2021/060913
§ 371 (c)(1),
(2) Date: May 18, 2023

(87) PCT Pub. No.: WO2022/118144
PCT Pub. Date: Jun. 9, 2022

(65) Prior Publication Data
US 2023/0404536 A1 Dec. 21, 2023

(30) Foreign Application Priority Data
Dec. 1, 2020 (IT) .................. 102020000029327

(51) Int. Cl.
*A61B 8/00* (2006.01)
*A61B 8/08* (2006.01)

(52) U.S. Cl.
CPC ............ *A61B 8/5207* (2013.01); *A61B 8/085* (2013.01); *A61B 8/5246* (2013.01)

(58) Field of Classification Search
CPC ...... A61B 8/5207; A61B 8/085; A61B 8/5246
See application file for complete search history.

(56) References Cited

U.S. PATENT DOCUMENTS 5,526,816 A * 6/1996 Arditi ................. G01S 7/52039
600/458
6,021,093 A * 2/2000 Birchak .................. G01V 1/44
181/105

(Continued)

FOREIGN PATENT DOCUMENTS

| JP | 2001238884 A | * | 9/2001 | |
| WO | WO-0185011 A2 | * | 11/2001 | ............. A61B 8/587 |

OTHER PUBLICATIONS

Taniguchi [ Differentiation of Renal Cell Carcinomas from Angiomyolipomas by Ultrasonic Frequency Dependent Attenuation, The Journal of Urology, vol. 157, 1242-1245, Apr. 1997], (Year: 1997).*

*Primary Examiner* — Oommen Jacob
(74) *Attorney, Agent, or Firm* — R. Ruschena Patent Agent, LLC

(57) ABSTRACT

An ultrasound device for carrying out a renal diagnostic examination for the diagnosis of renal cell carcinoma, comprising at least an ultrasound probe and relative control means, acquiring and storing means of the ultrasonic signals reflected by the tissues, it is configured to carry out the following acquisition procedure: —transmitting at least one broadband ultrasonic pulse beam towards the patient's kidney, receiving and storing the raw ultrasonic signals reflected by the renal tissue and processing said signals to obtain a renal ultrasound image, —while keeping the probe in the same position, transmitting a narrow band ultrasonic pulse beam towards the patient's kidney, receiving and storing the ultrasonic signals reflected by the renal tissue in response to the narrow band ultrasonic pulse beam sent at point 130), and characterized in that it is configured to carry out a calculation method of a diagnostic parameter.

9 Claims, 4 Drawing Sheets

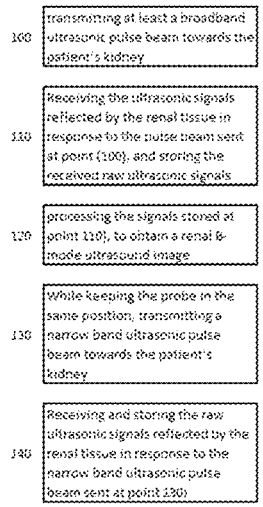

(56) References Cited

U.S. PATENT DOCUMENTS

| | | | | |
|---|---|---|---|---|
| 9,492,139 | B2* | 11/2016 | Rosen | A61B 8/00 |
| 10,327,740 | B2* | 6/2019 | Insana | A61B 8/5269 |
| 2002/0099286 | A1* | 7/2002 | Sandler | A61M 1/3656 |
| | | | | 600/407 |
| 2004/0054281 | A1* | 3/2004 | Adam | G01S 7/52077 |
| | | | | 600/437 |
| 2008/0091125 | A1* | 4/2008 | Owen | A61N 7/02 |
| | | | | 601/4 |
| 2009/0036772 | A1* | 2/2009 | Lu | G01S 15/8977 |
| | | | | 600/437 |
| 2009/0136057 | A1* | 5/2009 | Taenzer | H04R 3/005 |
| | | | | 381/74 |
| 2010/0145196 | A1* | 6/2010 | Cerofolini | A61B 8/481 |
| | | | | 600/458 |
| 2012/0232388 | A1* | 9/2012 | Curra | A61B 8/466 |
| | | | | 600/438 |
| 2013/0023767 | A1* | 1/2013 | Mammone | A61B 8/14 |
| | | | | 600/443 |
| 2014/0066767 | A1* | 3/2014 | Mammone | A61B 8/0825 |
| | | | | 600/443 |
| 2018/0085605 | A1* | 3/2018 | Maharbiz | A61B 5/0031 |
| 2023/0404536 | A1* | 12/2023 | Casciaro | A61B 8/5207 |

* cited by examiner

| | |
|---|---|
| 100 | transmitting at least a broadband ultrasonic pulse beam towards the patient's kidney |
| 110 | Receiving the ultrasonic signals reflected by the renal tissue in response to the pulse beam sent at point (100), and storing the received raw ultrasonic signals |
| 120 | processing the signals stored at point 110), to obtain a renal B-mode ultrasound image |
| 130 | While keeping the probe in the same position, transmitting a narrow band ultrasonic pulse beam towards the patient's kidney |
| 140 | Receiving and storing the raw ultrasonic signals reflected by the renal tissue in response to the narrow band ultrasonic pulse beam sent at point 130) |

Fig. 1

| | |
|---|---|
| 200 | analysis of the ultrasound image obtained at point 120) in order to identify one or more suspicious regions by analyzing the statistical distribution of the coefficients of the wavelet transform associated with the reflected ultrasonic signal stored at point 110) |
| 210 | Extraction from said raw ultrasonic signals reflected by the renal tissue in response to the narrow band ultrasonic pulse beam of the signal relating to at least a segment contained in the suspect region |
| 220 | execution of the frequency transform of the signal extracted at point 210) |
| 230 | extraction from said spectrum calculated at point 220) of the values relating to a plurality of significant frequencies |
| 240 | Extraction from said raw ultrasonic signals reflected by the renal tissue in response to the broadband signals of the signal relating to at least a segment contained in the suspect region |
| 250 | calculation of the frequency transform of the signal extracted at point 240) |
| 260 | Extraction from said spectrum calculated at point 250) of one or more descriptive parameters |
| 270 | Calculation of a diagnostic parameter indicating the tumor presence and type (renal cell carcinoma, benign tumor) as a function of said values extracted at point 230) and of said descriptive parameters calculated at point 260) |

Fig.2

| 550 | for each one of the descriptors calculated at points 520) to 540), realization of an image obtained by associating the value of the descriptor to the point of the ultrasound image associated to the window the descriptor was calculated for |

| 560 | analysis of each of said images obtained at point 550) to individuate one or more not homogeneous regions with respect to the surrounding region |

| 570 | Comparison of the inhomogeneities individuated at point 560) with the relative portion of ultrasound image |

Fig.3

| | |
|---|---|
| 400 | For each segment of a propagation line of the ultrasonic signal contained inside the renal tissue |
| 401 | Decomposition of the raw ultrasonic signal reflected by the segment by means of DWPT transform |
| 402 | Calculation of DWPT coefficient associated to each band for each point of the segment considered, thus defining a set of coefficients for each of said points |
| 403 | Calculation of at least a statistical descriptor chosen among: average value, median value, modal value, minimum value, maximum value, standard deviation, skewness, kurtosis |
| 410 | Definition of a series of parameters relating to a generic segment of a propagation line of the ultrasonic signal contained inside the renal tissue |
| 420 | Training of a classification neural network, by using a set of data containing the parameters defined at point 400 for a plurality of regions for which the result of the carcinoma has been confirmed by subsequent histological examination and for a plurality of regions relating to a homogeneous healthy renal tissue |
| 430 | Presentation to the trained network of the set of data relating to each not homogeneous region individuated at step 340 |
| 440 | Classification of the not homogeneous region as renal cell carcinoma or as healthy tissue, as a function of the network output |

Fig.4

METHOD FOR RENAL CELL CARCINOMA DIAGNOSIS BY MEANS OF ULTRASONIC SIGNALS ANALYSIS AND ULTRASOUND IMAGES

BACKGROUND OF THE INVENTION

1. Field of the Invention

The present invention relates to a method for the diagnosis of a renal cell carcinoma by means of ultrasonic signals analysis and ultrasound images.

2. Brief Description of the Prior Art

The increasing use of diagnostic imaging has led to an increased detection of various lesions and/or abnormal masses, often discovered casually thanks to tests carried out for other reasons (incidentalomas).

Anyway, since many lesions found out incidentally will never be able to cause any disease, finding incidentalomas increases the risk of overdiagnosis. When an incidentaloma is discovered, the clinician has to verify that this lesion is not very dangerous, and so he could carry out other tests to determine the nature of the lesion.

The distinction between tumor masses and benign masses is particularly difficult in case of renal masses.

According to Oostenbrugge et al "Diagnostic Imaging for solid renal tumors: a pictorial review", Kidney Cancer 2 (2018) 79-93, 20% of renal tumors discovered accidentally are benign lesions and do not require following treatments, but the most of them are renal cell carcinomas requiring an aggressive therapeutic approach.

So, it is clearly fundamental a diagnostic method that is effective in determining if a renal lesion is to be considered malign or not, and that at the same time is inexpensive, rapid and not invasive for the patient.

Among the diagnostic imaging techniques, the one by means of ultrasounds is well-known for a plurality of different test types.

With reference to the ultrasound scan for renal tumors diagnosis classification, according to what known at the state of the art, the trans-abdominal B-mode ultrasound with frequencies between 3 and 6 MHz is used.

The patient lays on owns back or is in the lateral decubitus position, and the kidneys are scanned in longitudinal and transversal direction through the sides.

The efficacy of the ultrasound investigation in detecting renal tumor depends on the tumor echogenicity, dimension and position.

During the ultrasound scan, hypoechoic (dark areas on the ultrasound images with respect to the surrounding renal parenchyma), hyperechoic (clear areas on the ultrasound images with respect to the surrounding renal parenchyma) or isoechoic renal tumors are detected, that are not detectable (or hardly detectable) by means of the grayscale analysis of the corresponding ultrasound images, since they are apparently similar to the surrounding renal parenchyma.

Isoechoic and hypoechoic tumors are more difficult to be detected by means of an ultrasound scan, in particular if they are smaller than 20 mm and are of isoechoic type. Moreover, even when tumor masses are detected, there remains the problem of their classification, intended as the distinction between renal cell carcinomas and benign masses (angiomyolipomas, oncocytomas, etc.). At the state of the art, it is known in fact that the tumor echogenicity cannot distinguish among histological sub-types, and so, benign tumors cannot be distinguished reliably from the malign ones.

It is also known the use of Doppler ultrasonography with or without contrast media, but also the efficacy of these techniques in characterizing a lesion as malign or benign has not been proved so far. Other methods of analysis of ultrasound images or ultrasonic signals aiming at improving tumor detection by means of ultrasound scan are known as well. In WO2018/157130, for example, a method is described to obtain an improved ultrasound image to allow a physician to formulate a diagnosis of liver or renal tumor only on the basis of ultrasound images.

Technical Problem

Anyway, this and other modes of ultrasound analysis known at the state of the art are limited for various reasons.

In prim is they do not allow to classify the various renal tumor histological types. In secundis they do not allow to detect effectively the isoechoic, hardly visible (or not visible at all) masses on the ultrasound image. Finally, they do not allow to prescind from the subjective analysis of the physician carrying out the ultrasound scan. Aim of the invention Aim of the present invention is to provide a diagnostic method for individuating renal tumor masses or for classifying their type, only based on the analysis of the ultrasound signal, which overcomes the limits linked to the embodiments known at the state of the art. In particular, a method which allows to detect effectively isoechoic masses as well, to classify the various histological types and that prescinds from the subjective analysis of the physician carrying out the ultrasound scan.

According to another aim, the present invention provides an ultrasound device configured to carry out such diagnostic method.

BRIEF DESCRIPTION OF THE DRAWINGS

In FIG. 1 is reported a block diagram showing the method for acquiring and elaborating ultrasound signals;

In FIG. 2 is reported a block diagram showing the method for calculating a diagnostic parameter;

In FIG. 3 is reported a block diagram showing further embodiments of the method for calculating a diagnostic parameter;

In FIG. 4 is reported a block diagram showing further embodiments of the method for calculating a diagnostic parameter.

DETAILED DESCRIPTION OF THE INVENTION

The invention will be now described with reference to the appended FIGS. 1 to 3 showing schematized flowcharts respectively relating to the acquiring procedure, to a diagnostic parameter calculation and to not homogeneous regions individuation by means of wavelet transforms analysis.

It is to be said at first that the proposed method relates to the analysis of ultrasound signals detected by means of a renal transabdominal ultrasound scan, carried out according to what commonly occurs at the state of the art concerning the acquiring positions.

Therefore, the acquiring positions and the ultrasound imaging planes are those commonly used.

In particular, according to what known and commonly applied, a preparation for a renal ultrasound scan is not needed, since there is no proved evidence that fasting can favour renal visibility.

The ultrasound scan is normally carried out in supine or oblique decubitus, by lifting the side under scan. In case of meteorism of colic flexures a rear approach can be needed with probe positioned at the posterior axillary line or even more dorsally. In these cases, the subcostal approach is not possible, and the renal scan has to be done by using the window of the intercostal spaces, that however do not allow a representation of the whole kidney on only one scan.

In children and thin people, a prone decubitus can be used, given the reduced thickness of dorsal paravertebral muscles.

These indications about the modes of choice of the ultrasound acquiring planes can be applied also to the ultrasound scan carried out with the device and method according to the invention.

The device according to the invention comprises at least an ultrasound probe, control means configured to guide said probe, acquiring and storing means of the ultrasonic signals reflected by tissues, processing means of the data relating to said signals configured to obtain a B-mode ultrasound image, and visualization means of the acquired image.

These are features yet provided in the devices known at the state of the art, and so they will not be described in more detail here.

The device according to the invention is characterized in that it is configured to acquire and store also the "raw" ultrasonic signals, also called radiofrequency ultrasonic signals (i.e. the ultrasonic signals as received by the probe, before their processing needed to obtain the ultrasound image), and to be provided with computing means on which suitable computer programs are loaded, that are configured to carry out the diagnostic method described in the following.

It is to be said at first that in the following it is described the acquisition of a renal ultrasound image, as well as the sending of ultrasonic signals towards the kidney.

It is clear that the ultrasonic signals will travel across propagation lines that, before reaching the kidney, go through a plurality of various tissues as a function of the acquiring position.

In a first embodiment, the selection of the signal relating to the region of interest relating to the kidney will be done by the expert in the field by means of tools known per se and known at the state of the art.

Preferably, the device according to the invention is configured to segment the acquired ultrasound image to determine the region of interest relating to the kidney automatically.

The device according to the invention is also configured to carry out, for each acquiring position, the following acquiring procedure of ultrasonic signals. To such aim, the device comprises electronic computing means on which computer programs are loaded, which are configured to carry out the method described in the following. 100) transmitting at least a broadband ultrasonic pulse beam towards the patient's kidney.

For clarity's sake it is to be specified that with ultrasonic pulse beam a group of pulses is intended, each emitted by a piezo-electric or CMUT transducer. It is to be specified in fact that also where the invention is described for brevity with reference to piezo-electric transducers, other transducers known at the state of the art can be used, as for example CMUT capacitive transducers. 110) Receiving the ultrasonic signals reflected by the renal tissue in response to the pulse beam sent at point (100), and storing the received raw ultrasonic signals;

120) processing the signals stored at point 110), to obtain a renal B-mode ultrasound image.

In the imaging step, the ultrasound probe works in broadband. When preferably a probe with nominal frequency equal to 3.5 MHz is used, the effective band is between 0 and 7 MHz.

130) While keeping the probe in the same position, transmitting a narrow band ultrasonic pulse beam towards the patient's kidney.

Preferably, the frequency used is a frequency near, but slightly lower than the probe nominal frequency. In case of using a probe with nominal frequency equal to 3.5 MHz, preferably the frequency used for narrow band pulse transmission is equal to 3 MHz.

It is to be specified that only the fact that the device is configured to carry out automatically the just described acquiring procedure allows to obtain the sending of broadband and narrow band signals in the same acquiring plane, since the narrow band signals can be sent immediately after the listening (i.e. receiving) time end of the broadband signals. This allows to carry out numerical analyses, in which the response both to broadband and narrow band pulses is known for sure for each portion of tissue.

140) Receiving and storing the raw ultrasonic signals reflected by the renal tissue in response to the narrow band ultrasonic pulse beam sent at point 130).

The device according to the invention is also configured to carry out, after the just described acquiring procedure, the calculation method of a diagnostic parameter, comprising the following steps of:

200) analysis of said raw ultrasonic signals reflected in response to said broadband pulse beam, stored at point 110) to individuate one or more suspect regions, by means of the analysis of the statistical distribution of the coefficients of the associated wavelet transform.

Said individuation can be possibly also carried out by the operator by means of a suitable graphical interface to analyze other suspect regions not identified by the analysis at point 200).

For each suspect region individuated at point 200) the following method is carried out, to calculate a diagnostic parameter indicating the presence of a renal tumor. 210) Extraction from said raw ultrasonic signals reflected by the renal tissue in response to the narrow band ultrasonic pulse beam, stored at point 140) of the signal relating to at least a segment contained in the suspect region;

220) execution of the frequency transform of the signal extracted at point 210), to calculate at least a frequency spectrum obtained in response to a narrow band ultrasonic signal. Preferably, said frequency transform is an FFT;

230) extraction from said spectrum calculated at point 220) of the values relating to a plurality of significant frequencies. Preferably, said frequencies comprise: the nominal frequency of the sent narrow band signal,
the first harmonic (that is twice as big as said nominal frequency of the sent narrow band signal); the first sub-harmonic of the signal (that is half said nominal frequency of the sent narrow band signal).

In case of narrow band signal with 3 MHz frequency, in a preferred embodiment, the three values extracted are then those relating to 1.5 MHz, 3 MHz, 6 MHz.

240) Extraction from said raw ultrasonic signals reflected by the renal tissue in response to the broadband signals stored at point 110) of the signal relating to at least a segment contained in the suspect region;

250) calculation of the frequency transform of the signal extracted at point 240) to obtain at least a frequency spectrum obtained in response to a broadband ultrasonic signal. Preferably, said frequency transform is an FFT.

260) Extraction from said spectrum calculated at point 250) of one or more descriptive parameters.

Preferably, the calculated parameters comprise one or more among the following ones:

spectrum average value;

region subtended by the spectrum in a determined frequency interval; spectrum width (intended as the difference between maximum and minimum frequency) at a predetermined intensity level, in particular at a level defined by an intensity value lower than the maximum value of said spectrum for a predetermined amount, in particular lower than 1 dB or 3 dB;

the frequency value corresponding to the maximum value of said spectrum; —the slope of a line interpolating a plurality of points of said spectrum in a predetermined frequency interval; the coefficients of a polynomial interpolating the points of said frequency spectrum in a frequency interval containing the maximum of said spectrum.

270) Calculation of a diagnostic parameter indicating the tumor presence and type (renal cell carcinoma, benign tumor) as a function of said values extracted at point 230) and of said descriptive parameters calculated at point 260).

It is to be observed that the diagnostic parameter calculated at point 270), in the various modes of calculation thereof, indicates not-linearities introduced in the ultrasonic spectrum reflected by the cell structure of the region under scan and by its possible distortions.

It is also to be observed that its calculation is possible only because, while the probe is in the same acquiring position, both the ultrasonic signals reflected upon transmission of a broadband signal (so that it is possible to obtain a significant ultrasound image, and so that it is possible to individuate hypoechoic and hyperechoic regions on the same) and the ultrasonic signals reflected upon transmission of a narrow band signal (in order to highlight the not-linearities introduced by the cell structure of the region of interest and by its possible distortions) have been acquired.

Preferably, said diagnostic parameter indicating the tumor type is obtained as a function of: the longitudinal dimension of said suspect region;

the transversal dimension of said suspect region;
the surface area of said suspect region;
the ratio between the surface area and length of said suspect region edges; the ratio between the intensity of the first harmonic ($\omega 1$) and the intensity of the nominal frequency ($\omega n$) of the frequency spectrum obtained in response to a narrow band ultrasonic signal calculated at point 220);
the ratio between the intensity of the first sub-harmonic ($\omega sub1$) and the intensity of the nominal frequency ($\omega n$) of the frequency spectrum obtained in response to a narrow band ultrasonic signal calculated at point 220);
said parameters extracted at point 260).

Moreover, preferably said diagnostic parameter indicating the tumor type is calculated by comparing the just described parameters with the similar ratios relating to ultrasonic signals corresponding to:

a plurality of regions, for which the result of the carcinoma has been confirmed by subsequent histological examination;

a plurality of regions relating to homogeneous, and reasonably healthy, renal tissue.

In the following, it is to be specified a preferred embodiment of the method for individuating masses not detectable by means of ultrasound imaging.

The biological tissues can be assimilated to an agglomerate of "scatterers" deployed irregularly, that generate not stationary signals. So, the signal spectral content is modified locally, and it is required a time-frequency representation (TFR), since TFR representations are able to identify the time intervals on the signal, in which specific spectral components are present. In particular, the wavelet transform (WT) expands the signals by means of wavelet functions localized both in time and frequency and offers the possibility of a flexible decomposition, which processes the signal with adjustable filter-windows on the basis of frequency, instead of processing the signal with a sliding window having time-constant length (as it occurs in case of FFT, which is actually a TFR with fixed resolution).

In this specific case, in order to individuate masses not detectable by means of ultrasound imaging, as a way of example, it is possible to use the specific technique of wavelet analysis known at the state of the art as DWPT (discrete wavelet packets transform), chosen to reduce computational costs and characterized, as a way of example, by the use of the following parameter configuration (which represents a suitable compromise between time resolution and frequency resolution): biorthogonal and symmetrical "mother-wavelet" function (ex. "Daubechies 16");

decomposition level: 3°
decimation level: 1°.

In said parameter configuration, by assuming that the "raw" ultrasonic signal was sampled at 40 MHz (40 MS/s), DWPT decomposes the signal corresponding to each considered propagation line in 8 frequency bands, which cover the whole spectral content range of the signal examined: 8 bands of 2.5 MHz amplitude, each one going from 0 to 20 MHz, which is half the sampling frequency used. In this way, for each "raw" ultrasonic signal (corresponding to a determined propagation line) 8 sets of DWPT coefficients are calculated; each set corresponds to a specific frequency band and in each set the DWPT coefficients are equal in number to the sampling instants considered (since the decimation was equal to 1, i.e. no decimation has been carried out).

In this way, at each time instant of the starting signal 8 DWPT coefficients have been associated (each relating to a specific one of said 8 frequency bands), which can be identified as kixy, wherein i identifies the frequency band, x identifies the signal considered (i.e. the propagation line) and y identifies the time instant considered (that corresponds actually to a certain distance from the probe and to a certain depth inside the tissue).

So: i varies between 1 and the number "n" of the frequency bands (for example 8, in case of third level wavelet decomposition);

x varies between 1 and the number of available propagation lines, which typically coincides with the number of piezoelectric transducers in the probe or with its double (ex. 128 or 256); —y varies between 1 and the number of samples the signal is made up of (a value that, once the sampling frequency is known, is determined by the acquiring depth set on the ultrasound device).

In other words, a number of klxy coefficients is associated at each point (x, y) of the ultrasound image, which is equal to the number of frequency bands.

So, the statistical distribution of the kixy coefficients in the various areas of the ultrasound image can be used to characterize the corresponding portions of renal tissue through the following steps.

At each step, as a way of example, it is referred also the description of a preferred and not limiting embodiment.

499) decomposition by means of DWPT wavelet transform of the "raw" ultrasonic broadband reflected signal received by each of said piezoelectric transducers in a plurality (n) of frequency bands, and calculation for each sampling instant of said signal of a plurality (n) of DWPT coefficients (kixy), 500) definition of a mobile analysis window in the ultrasound image plane, 510) definition of an advancement step of said mobile analysis window for each of the two directions, 520) with the mobile window positioned in a first position of the ultrasound image:

521) identification of the values of said DWPT coefficients (kixy) associated to each one of the points contained inside said mobile window, thus defining a plurality (n) of sets of DWPT coefficients associated to the specific position of the window;

522) calculation, for each set of DWPT coefficients defined at point 521), of at least a statistical descriptor chosen among: average value, median value, modal value, minimum value, maximum value, standard deviation, skewness, kurtosis.

Preferably, for each set of DWPT coefficients, calculation of a plurality "m" of enlisted descriptor (for example the enlisted 8). At each window position it is then possible to calculate "n×m" statistical descriptors (64 in the case of example).

530) Advancement of the window defined at point 500) along one of the two advancement directions by an amount equal to the respective step defined at point 510) 540) repetition of steps 520) to 530), with advancements along the one or the other direction, until the whole region of interest, coincident with the kidney, has been covered by the mobile acquiring window.

For clarity's sake, it is to be said again that the region of interest can be identified both manually and by means of automatic identification algorithms.

For each one of the "m×n" descriptors calculated, it is then obtained a value associated to each point of the ultrasound image, contained in the region of interest (the point, the descriptor value is associated to, is the central point of the mobile window in the position the descriptor was calculated for). So, "m×n" maps, each relating to one specific descriptor, have been obtained.

550) For each one of the descriptors calculated at points 520) to 540), realization of an image obtained by associating the value of the descriptor to the point of the ultrasound image associated to the window the descriptor was calculated for;

560) analysis of each of said images obtained at point 550) to individuate one or more not homogeneous regions with respect to the surrounding region. Said individuation can be carried out by the operator, by means of a suitable graphical interface, or can be carried out automatically by means of suitable segmentation algorithms.

570) Comparison of the inhomogeneities individuated at point 560) with the relative portion of ultrasound image. In case the presence of inhomogeneities is not justified by anatomical differences visible on the ultrasound image (which instead in that region does not have any apparent peculiarity), identification of the corresponding portion of tissue as suspect region to be classified. So, these not homogeneous regions, or suspect regions, can be classified as relating to a healthy tissue or as relating to renal cell carcinomas, according to the method described at steps 210) to 240).

The extension of these regions and their classification can be shown superimposed on the ultrasound image, by using a suitable color mapping to be superimposed on the conventional greyscale B-mode ultrasound image.

It is to be noted that only the joined, and for the same position, acquisition of:
ultrasound image,
raw broadband radiofrequency ultrasonic signal,
raw narrow band radiofrequency ultrasonic signal allows to implement the just described method.

According to another embodiment, in order to calculate the diagnostic parameter of point 270), the procedure can be as follows:

400) for each segment of a propagation line of the ultrasonic signal contained inside the renal tissue:

401) decomposition of the raw ultrasonic signal reflected by the segment by means of DWPT transform (discrete wavelet packets transform);

402) calculation of the values the DWPT coefficient associated to each band assumes for each one of the points of the segment considered, thus defining a set of coefficients for each of said points;

403) calculation, for each set of DWPT coefficients defined at point 402), of at least a statistical descriptor chosen among: average value, median value, modal value, minimum value, maximum value, standard deviation, skewness, kurtosis;

410) definition of a series of parameters relating to a generic segment of a propagation line of the ultrasonic signal contained inside the renal tissue, comprising: at least one of the statistical descriptors calculated at point 522) and associated to the segment of propagation line examined; the ratio between the intensity of the first harmonic ($\omega 1$) and the intensity of the nominal frequency ($\omega n$) of the narrow band radiofrequency reflected raw ultrasonic signal;

the ratio between the intensity of the first subharmonic (cosub1) and the intensity of the nominal frequency ($\omega n$) of the narrow band radiofrequency reflected raw ultrasonic signal;

the average value of the frequency spectrum of the broadband radiofrequency reflected raw ultrasonic signal;

the region subtended by the frequency spectrum of the broadband reflected raw ultrasonic signal in a determined frequency interval and/or in a determined amplitude interval; spectrum width (intended as the difference between maximum and minimum frequency) at a predetermined intensity level, in particular at a level defined by an intensity value lower than the maximum value of said spectrum for a predetermined amount, in particular lower than 1 dB or 3 dB;

the frequency value corresponding to the maximum value of said frequency spectrum of the broadband reflected raw ultrasonic signal;

the slope of a line interpolating a plurality of points of said frequency spectrum of the broadband reflected raw ultrasonic signal in a predetermined frequency interval;

the coefficients of a polynomial interpolating the points of said frequency spectrum of the broadband reflected raw ultrasonic signal in a frequency interval containing the maximum of said spectrum.

420) Training of a classification neural network, by using a set of data containing the parameters defined at point 400) for a plurality of regions for which the result of the carcinoma has been confirmed by subsequent histological examination and for a plurality of regions relating to a homogeneous, and reasonably healthy renal tissue.

430) Presentation to the trained network of the set of data relating to each not homogeneous region individuated at point 340).

440) Classification of the not homogeneous region as renal cell carcinoma or as healthy tissue, as a function of the network output.

In another embodiment, a convolutional neural network can be trained, by using a plurality of said images obtained at point 550), and of the corresponding ultrasound images relating to patients for whom the result of the carcinoma has been confirmed by subsequent histological examination and for a plurality of images relating to a homogeneous, and reasonably healthy renal tissue.

The invention claimed is:

1. An ultrasound device for carrying out a renal diagnostic examination for a diagnosis of renal cell carcinoma, comprising:
   at least one ultrasound probe, comprising a plurality of piezoelectric or CMUT transducers,
   control device configured to drive said probe, for acquiring and storing ultrasonic signals reflected by tissues, configured to store also raw ultrasonic signals as received by said probe, before the processing steps to obtain the B-mode ultrasound image, wherein it is configured to carry out the following acquisition steps:
   100) transmitting at least one broadband ultrasonic pulse beam towards a patient's kidney;
   110) receiving the ultrasonic signals reflected by the renal tissue in response to said pulse beam sent at step 100), and storing the received raw ultrasonic signals;
   120) processing said ultrasonic signals stored at step 110), to obtain a renal B-mode ultrasound image 130) while keeping the probe in a same position, transmitting a narrow band ultrasonic pulse beam towards the patient's kidney;
   140) receiving and storing the raw ultrasonic signals reflected by the renal tissue in response to the narrow band ultrasonic pulse beam sent at step 130), and wherein it comprises also a computing device on which suitable computer programs are loaded, which are configured to carry out a calculation method of a diagnostic parameter, comprising the following steps:
   200) analyzing of said raw ultrasonic signals reflected in response to said broadband pulse beam, stored at step 110) to individuate one or more suspect regions, using the analysis of a statistical distribution of coefficients of an associated wavelet transform, for each suspect region:
   210) extracting from said raw ultrasonic signals reflected by the renal tissue in response to the narrow band ultrasonic pulse beam, stored at step 140) of the signal relating to at least one segment contained in the suspect region;
   220) executing of a frequency transform of signals extracted at steps 210), 230) extraction from a spectrum calculated at step 220) of values relating to a plurality of significant frequencies;
   240) extracting from said raw ultrasonic signals reflected by the renal tissue in response to broadband signals stored at step 110) of the signal relating to at least one segment contained in the suspect region;
   250) calculating of a frequency transform of the signal extracted at step 240) to obtain at least one frequency spectrum obtained in response to said at least one broadband ultrasonic pulse;
   260) calculating of one or more descriptive parameters of the spectrum calculated at step 250),
   270) calculating of a diagnostic parameter indicating a tumor presence and type as a function of said values extracted at step 230) and of said descriptive parameters calculated at step 260).

2. The ultrasound device according to claim 1, wherein said significant frequencies of step 230) comprise:
   a nominal frequency of said narrow band signal;
   a first harmonic of said nominal frequency;
   a first sub-harmonic of said nominal frequency.

3. The ultrasound device according to claim 1, wherein said diagnostic parameter calculated at step 270) is obtained as a function of one or more of the following parameters:
   longitudinal dimension of said suspect region;
   transversal dimension of said suspect region;
   a surface area of said suspect region; ratio between the surface area and length of said suspect region edges; ratio between an intensity of a first harmonic ($\omega 1$) and an intensity of a nominal frequency ($\omega n$) of the frequency spectrum obtained in response to a narrow band ultrasonic signal calculated at step 220);
   ratio between the intensity of the first subharmonic (co-sub1) and the intensity of the nominal frequency ($\omega n$) of the frequency spectrum obtained in response to a narrow band ultrasonic signal calculated at step 220);
   said parameters extracted at step 260).

4. The ultrasound device according to claim 3, wherein said diagnostic parameter is calculated by comparing said parameters with analogous parameters related to ultrasonic signals corresponding to:
   a plurality of regions, for which a carcinoma outcome has been confirmed by subsequent histological examination; a plurality of regions relating to a homogeneous, and reasonably healthy, renal tissue.

5. The ultrasound device according to claim 2, wherein the nominal frequency of said probe is equal to 3.5 MHZ, an effective band used for broadband acquisition is between 0 and 7 MHz and the frequency used for the transmission of narrow band pulses is equal to 3 MHZ.

6. The ultrasound device according to claim 1, wherein said suspect regions are hypoechoic or hyperechoic regions with respect to a surrounding renal parenchyma.

7. The ultrasound device according to claim 6, wherein said individuation of said suspect regions is obtained by the method according to the following steps:
   499) decomposing by means of DWPT wavelet transform of the "raw" ultrasonic broadband reflected signal received by each of said piezoelectric or CMUT transducers in a plurality (n) of frequency bands, and calculation for each sampling instant of said signal of a plurality (n) of DWPT coefficients (kixy),
   500) defining a mobile analysis window in the ultrasound image plane,
   510) defining an advancement step of said mobile analysis window for each of two directions,
   520) with said mobile analysis window positioned in a first position of the ultrasound image:

521) identifying values of said DWPT coefficients (kixy) associated to each one of the points contained inside said mobile window, thus defining a plurality (n) of sets of DWPT coefficients associated to the specific position of the window;

522) calculating, for each set of DWPT coefficients defined at step 521), of at least one statistical descriptor chosen among: average value, median value, modal value, minimum value, maximum value, standard deviation, skewness, kurtosis, 530) advancing said mobile analysis window defined at step 500) along one of the two advancement directions by an amount equal to the respective step defined at step 510), 540) repeating steps from 520) to 530), with advancements along the one or the other direction, until the whole region of interest, coincident with the kidney, has been covered by a mobile acquisition window;

550) for each one of the descriptors calculated at steps 520) to 540), realizing an image obtained by associating the value of the descriptor to the point of the ultrasound image associated to the window the descriptor was calculated for;

560) analyzing each of said images obtained at step 550) to individuate one or more not homogeneous regions with respect to the surrounding region.

8. The ultrasound device according to claim 1, wherein said descriptive parameters calculated at step 260) comprise one or more of the following parameters: —spectrum average value;

area subtended by a spectrum in a determined frequency interval; spectrum width at a predetermined intensity level;

frequency corresponding to the maximum value of said spectrum; slope of a line interpolating a plurality of points of said spectrum in a predetermined frequency interval;

coefficients of a polynomial interpolating the points of said frequency spectrum in a frequency interval containing the maximum of said spectrum.

9. The ultrasound device according to claim 1, wherein said diagnostic parameter of step 270) is calculated using the following steps of:

410) defining a series of parameters relating to a generic segment of a propagation line of the ultrasonic signal contained inside the renal tissue, comprising: at least one of the statistical descriptors calculated at step 522) and associated to the segment of propagation line examined; the ratio between the intensity of the first harmonic ($\omega 1$) and the intensity of the nominal frequency ($\omega n$) of said raw ultrasonic signals as received by said probe; the ratio between the intensity of the first sub-harmonic ($\omega sub1$) and the intensity of the nominal frequency ($\omega n$) of the raw ultrasonic signal reflected in response to a narrowband pulse;

the average value of the frequency spectrum of the raw ultrasonic signal reflected in response to a broadband pulse;

area subtended by the frequency spectrum of the broadband reflected raw ultrasonic signal in a determined frequency interval and/or in a determined amplitude interval; spectrum width at a predetermined intensity level, frequency corresponding to the maximum value of said frequency spectrum of the broadband reflected raw ultrasonic signal; slope of a line interpolating a plurality of points of said frequency spectrum of the broadband reflected raw ultrasonic signal in a predetermined frequency interval;

the coefficients of a polynomial interpolating the points of said frequency spectrum of the broadband reflected raw ultrasonic signal in a frequency interval containing the maximum of said spectrum, 420) training of a neural network, by using a set of data containing the parameters defined at step 400) relating to a plurality of regions for which the result of the renal cell carcinoma has been confirmed by subsequent histological examination and for a plurality of regions relating to a homogeneous, and reasonably healthy, renal tissue;

430) presenting to said neural network of the set of data relating to each not homogeneous region individuated at a step 340), 440) classifying the not homogeneous region as renal cell carcinoma or as healthy tissue, as a function of the network output.

* * * * *